(12) United States Patent
Ben-Shmuel et al.

(10) Patent No.: US 11,913,639 B2
(45) Date of Patent: Feb. 27, 2024

(54) LIGHTING SYSTEMS FOR GENERAL ILLUMINATION AND DISINFECTION

(71) Applicant: JUGANU LTD., Rosh Haain (IL)

(72) Inventors: Eran Ben-Shmuel, Rosh Haain (IL); Ada Lotan, Rosh Haain (IL); Alexander Bilchinsky, Rosh Haain (IL); Eran Efrati, Rosh Haain (IL); Jonathan Stok, Rosh Haain (IL); Yossi Bechor, Rosh Haain (IL); Yoav Bar, Rosh Haain (IL); Noam Meir, Rosh Haain (IL)

( * ) Notice: Subject to any disclaimer, the term of this patent is extended or adjusted under 35 U.S.C. 154(b) by 56 days.

(21) Appl. No.: 17/845,299

(22) Filed: Jun. 21, 2022

(65) Prior Publication Data

US 2022/0325870 A1 Oct. 13, 2022

Related U.S. Application Data

(63) Continuation of application No. 17/209,435, filed on Mar. 23, 2021, now Pat. No. 11,391,439, which is a continuation-in-part of application No. 16/850,760, filed on Apr. 16, 2020, now Pat. No. 11,006,493, said application No. 16/850,760 is a continuation-in-part of application No. 16/750,031, filed on Jan. 23, 2020, which is a continuation of application No. 16/425,083, filed on May 29, 2019, now Pat. No. 10,582,586.

(60) Provisional application No. 62/993,295, filed on Mar. 23, 2020, provisional application No. 62/811,551, filed on Feb. 28, 2019, provisional application No. 62/677,405, filed on May 29, 2018.

(30) Foreign Application Priority Data

Aug. 24, 2020 (GB) .................................. 2013198

(51) Int. Cl.
| | |
|---|---|
| *H05B 45/20* | (2020.01) |
| *F21V 9/30* | (2018.01) |
| *F21K 9/64* | (2016.01) |
| *F21K 9/68* | (2016.01) |
| *F21V 8/00* | (2006.01) |

(52) U.S. Cl.
CPC .................. *F21V 9/30* (2018.02); *F21K 9/64* (2016.08); *F21K 9/68* (2016.08); *G02B 6/0073* (2013.01); *H05B 45/20* (2020.01)

(58) Field of Classification Search
CPC ....... H05B 45/20; F21V 9/30; F21Y 2113/13; F21Y 2115/10; F21K 9/64; F21K 9/68; G02F 1/33621; G02F 1/133614; G02F 2203/05; G02B 6/0073; H01L 33/502; H01L 33/56

See application file for complete search history.

(56) References Cited

U.S. PATENT DOCUMENTS

| | | |
|---|---|---|
| 3,174,189 A | 3/1965 | Cutler et al. |
| 8,174,189 B2 | 5/2012 | Kim et al. |
| 8,858,836 B2 | 10/2014 | Duan et al. |
| 9,012,937 B2 | 4/2015 | Keller et al. |

(Continued)

*Primary Examiner* — Haissa Philogene
(74) *Attorney, Agent, or Firm* — Intrinsic Law Corp.

(57) ABSTRACT

Lighting systems combine UV-A and white light with an adjustable CCT value so that any adverse effects from the UV-A radiation are mitigated—that is, tunable adjustments to the output of the non-UV LEDs, or to all of the LEDs, result in an overall mixed output conforming to a target CCT value.

19 Claims, 15 Drawing Sheets

(56) References Cited

U.S. PATENT DOCUMENTS

| | | |
|---|---|---|
| 9,101,036 B2 | 8/2015 | Guzan et al. |
| 9,537,112 B2 | 1/2017 | Li et al. |
| 9,560,714 B1 | 1/2017 | Hjerde |
| 9,877,370 B2 | 1/2018 | Peeters et al. |
| 9,974,138 B2 | 5/2018 | Allen et al. |
| 9,976,710 B2 * | 5/2018 | Meir .................. H05K 3/361 |
| 10,165,735 B1 | 1/2019 | Carlie et al. |
| 10,582,586 B2 | 3/2020 | Meir |
| 10,925,134 B2 | 2/2021 | Meir |
| 11,006,493 B1 | 5/2021 | Meir et al. |
| 11,391,439 B2 * | 7/2022 | Ben-Shmuel ....... F21V 33/0064 |
| 2004/0052076 A1 | 3/2004 | Mueller et al. |
| 2008/0023712 A1 | 1/2008 | Mueller et al. |
| 2008/0203892 A1 * | 8/2008 | Schmidt ............. C09K 11/7731 |
| | | 252/301.4 R |
| 2012/0001555 A1 * | 1/2012 | Tu ..................... H05B 45/37 |
| | | 315/161 |
| 2013/0025865 A1 | 1/2013 | Knobloch, Jr. et al. |
| 2013/0154519 A1 | 6/2013 | Riesebosch |
| 2014/0035472 A1 * | 2/2014 | Raj ..................... H05B 45/22 |
| | | 315/297 |
| 2016/0030609 A1 | 2/2016 | Peterson et al. |
| 2018/0014374 A1 | 1/2018 | Rhodes et al. |
| 2018/0019350 A9 | 1/2018 | Kim et al. |
| 2018/0318599 A1 | 11/2018 | Van Bommel et al. |
| 2019/0011091 A1 * | 1/2019 | Meir .................. H05K 3/361 |
| 2019/0021695 A1 | 1/2019 | Watts et al. |
| 2019/0037370 A1 | 1/2019 | Beller et al. |
| 2019/0093832 A1 | 3/2019 | Soer et al. |
| 2019/0224350 A1 | 7/2019 | Marry et al. |
| 2019/0247528 A1 | 8/2019 | Rodriguez |
| 2020/0236760 A1 | 7/2020 | Meir |
| 2021/0205487 A1 | 7/2021 | Balme |

\* cited by examiner

LIGHTING SYSTEMS FOR GENERAL ILLUMINATION AND DISINFECTION

CROSS-REFERENCE TO RELATED APPLICATIONS

This application is a continuation of U.S. patent application Ser. No. 17/209,435, filed Mar. 23, 2021, which claims priority to and the benefits of, and incorporates herein by reference in their entireties, U.S. Provisional Application No. 62/993,295, filed on Mar. 23, 2020, and UK Patent Application No. 2013198.3, filed on Aug. 24, 2020. U.S. patent application Ser. No. 17/209,435 is also a continuation-in-part of U.S. Ser. No. 16/850,760, filed on Apr. 16, 2020, which is a continuation-in-part of U.S. Ser. No. 16/750,031, filed on Jan. 23, 2020, which is itself a continuation of U.S. Ser. No. 16/425,083, filed on May 29, 2019, which claimed priority to U.S. Provisional Application Nos. 62/811,551 (filed Feb. 28, 2019) and 62/677,405 (filed May 29, 2018). The entire disclosures of all of the foregoing documents are hereby incorporated by reference.

TECHNICAL FIELD

The present invention relates generally to lighting systems, and in various embodiments to systems for providing mixed light for illumination, protection from pathogens, and disinfection.

BACKGROUND

It is known that certain wavelength ranges of light, particularly ultraviolet (UV) light, are germicidal—i.e., capable of killing or inactivating pathogens such as bacteria, molds, spores and viruses, rendering them incapable of causing disease. Illumination devices emitting germicidal light are frequently used to decontaminate medical tools and environmental surfaces. UV radiation is dangerous to humans, and some wavelength bands are more dangerous than others. As a result, broadband germicidal UV applications are typically deployed in oven-like devices that receive items to be decontaminated and are closed when the radiation is activated, thereby shielding personnel from harm. Although automated UV-based room-decontamination systems have been developed, these generally are not used when people are present. See, e.g., Livingston et al., "Efficacy of an ultraviolet-A lighting system for continuous decontamination of health care-associated pathogens on surfaces," *Am. J. Infection Control*, 48:337-339 (2020). Unfortunately, recontamination can occur quickly following device operation once people return and resume their activities.

The most effective germicidal wavelength band, UV-C (100-280 nm), is also the most dangerous to humans. The UV-A band (315-400 nm), on the other hand, can be safe for use in limited doses and radiant flux, when people are present, and is known to have antimicrobial activity. Accordingly, it is possible to safely integrate UV-A lighting with general illumination, but the lighting sources used for these different wavelength ranges are different. Their outputs must be combined in a manner that preserves the quality of ambient light for affected personnel while ensuring safety.

SUMMARY

An increasing number of light fixtures utilize LEDs as light sources due to their lower energy consumption, smaller size, improved robustness, and longer operational lifetime relative to conventional filament-based light sources. Conventional LEDs emit light at a particular wavelength, ranging from, for example, red to UV light. However, for purposes of general illumination, the monochromatic emitted light by LEDs must be converted to broad-spectrum white light.

Embodiments of the present invention combine UV-A and white light with an adjustable CCT value so that any adverse effects from the UV-A radiation are mitigated—that is, tunable adjustments to the output of the non-UV LEDs, or to all of the LEDs, result in an overall mixed output conforming to a target CCT value. In one embodiment, the LED illumination device employs an LED array having multiple LEDs that can be controlled individually or in a group to generate white light having a tunable CCT value within a range. Optionally, each of the LEDs may be disposed within a "cup-shaped" (e.g., parabolic) reflector for reducing "crosstalk" interactions between the light emitted from an LED and the photoluminescent material(s) disposed above a neighboring LED. In addition, the reflector may be made of a high-reflectivity material so as to redirect upward light from the respective LED, thereby achieving at least partial collimation of the beam. The LEDs may operate in a normal mode in which only some UV-A LEDs are active and produce UV radiation at a level harmless to humans, while the other LEDs are operated to provide general illumination; and in a "boost" mode in which red and UV-A LEDs are active and the latter are operated at maximum power.

In various embodiments, the LEDs and/or photoluminescent material(s) are encapsulated within a waveguide material made of, e.g., silicone. Light emitted from the LEDs, including unconverted light and light converted by the photoluminescent material(s), can be mixed in a mixing region inside the waveguide and then directed to an output region for outputting white light for illumination. The illumination device may also include control circuitry for varying a parameter (e.g., the amplitude and/or duty cycle of the applied current or voltage) associated with each LED (or, in some embodiments, each group of the LEDs), thereby adjusting the CCT value of the mixed light to a target value.

The term "color" is used herein to denote the monochromatic or peak wavelength (or wavelengths) of light emitted by one or more LEDs. In addition, the term "uniform," as used herein, refers to a light intensity distribution whose lower and upper intensity limits are within a factor of four, preferably within a factor of two of each other. As used herein, the terms "approximately," "roughly," and "substantially" mean ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1A:
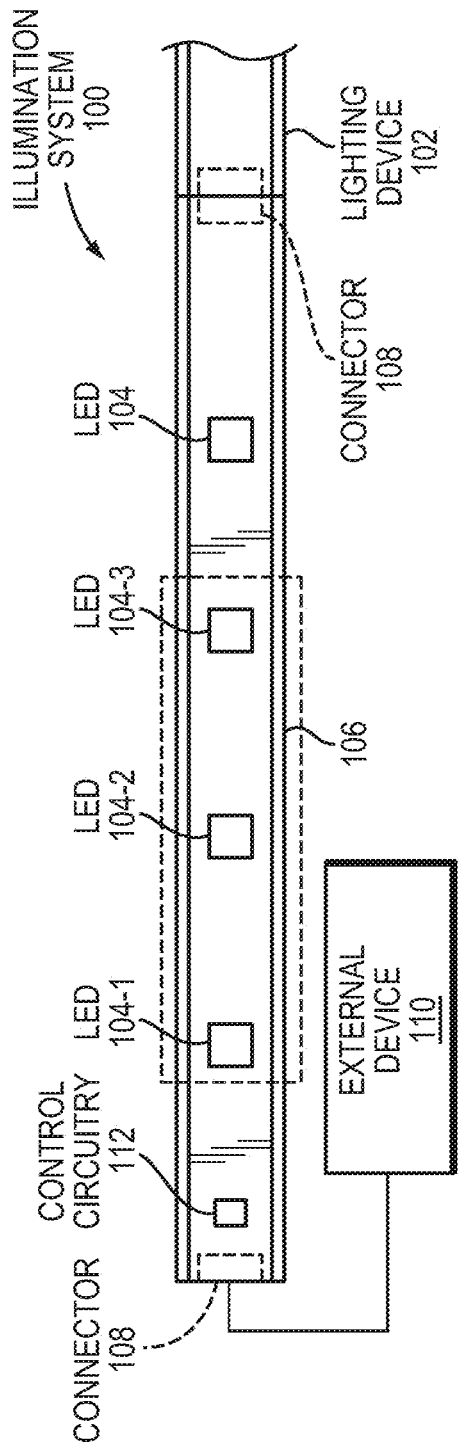
FIGS. 1A and 1B depict a top view and a bottom view, respectively, of an example illumination system in accordance with various embodiments.

FIG. 1A conceptually illustrates an exemplary illumination module 100 suitable for use in connection with various embodiments. Each module 100 includes one or more strip lighting devices 102; each strip 102 has an array of multiple LEDs 104 mounted to a circuit board 106 (e.g., printed circuit board, PCB). Each of the LED groups 104 may include one or more LED dies for emitting light with the same or different characteristics (e.g., colors, powers and/or CCT values). The LEDs 104 may be electrically coupled, via the circuit board 106, to connectors 108 mounted on each end of the circuit board 106. The connectors 108 may then electrically couple the LEDs 104 to an external device 110 (e.g., another lighting device, a dimming device, a power supply, an "Internet of things" (IoT) device, or a combination thereof) such that the LEDs 104 may receive power from the external device 110 via the connectors 108 and emit light.

In some embodiments, the LEDs 104 are electrically coupled to control circuitry 112 in the strip lighting device(s) 102. The control circuitry 112 may be configured to control operation of the LEDs 104 (e.g., by regulating the amplitude and/or duty cycle of the current and/or voltage applied to the LEDs 104), thereby regulating a characteristic (e.g., intensity or brightness) of the light emitted from the LEDs 104. For example, the control circuitry 112 may adjust the brightness of individual LEDs using pulse width modulation (PWM). For example, the control circuitry 112 may rapidly turn individual LEDs on and off at a high frequency that is imperceptible to humans. In this example, the brightness of the individual LEDs 104 may be changed by adjusting the ratio of on-time to off-time within a particular cycle (sometimes referred to as a "duty cycle"). The higher the ratio of on-time to off-time, the brighter the LED. Conversely, lowering the ratio of on-time to off-time dims the LED. Thus, the duty cycle may positively correlate to the average flux of the LED being controlled. The control circuitry 112 may vary the ratio of on-time to off-time based on control signals received from the external device 110 via the connectors 108. In one embodiment, the control circuitry 112 is implemented in circuitry that is external to the illumination system 100. For example, circuitry in the external device 100 may be configured to regulate the current and/or voltage applied to the LEDs 104, thereby directly controlling operations thereof. In this case, the control circuitry 112 may be omitted from the illumination system 100 altogether.

Figure 1B:
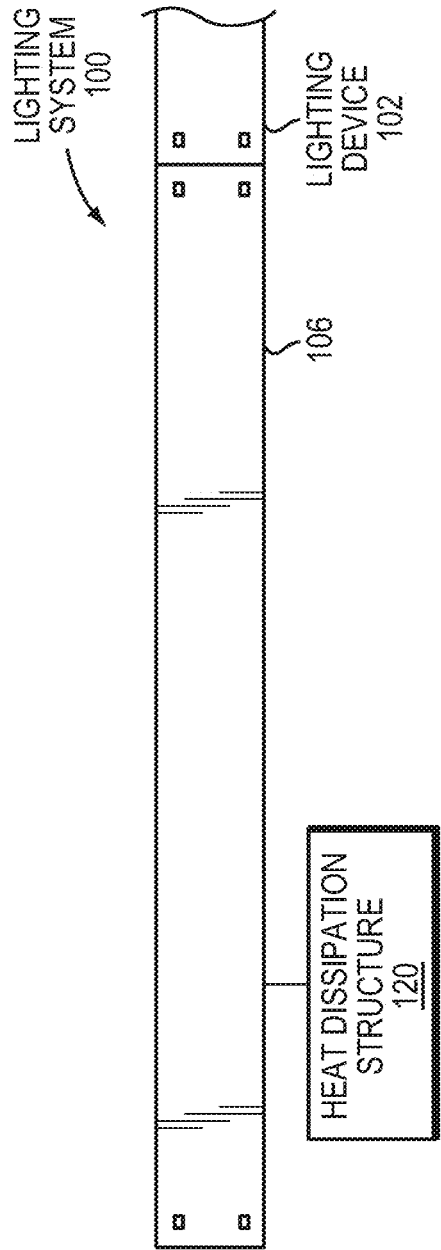

The LEDs 104, control circuitry 112, and/or the connectors 108 may be all mounted to the circuit board 106. For example, the circuit board 106 may include one or more conductors to electrically couple the components mounted thereto. In addition, the circuit board 106 may be flexible to enable the illumination system 100 to conform to uneven surfaces. Referring to FIG. 1B, in some embodiments, the bottom surface of the circuit board 106 is connected to a heat dissipation structure 120 (e.g., a conventional heat sink) for dissipating heat generated by the LEDs 104.

Figure 1C:
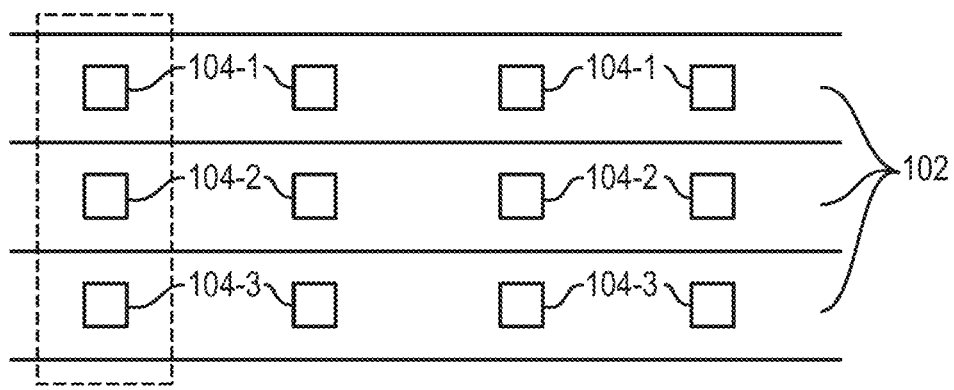
FIGS. 1C and 1D depict exemplary configurations of the LEDs in an illumination system in accordance with various embodiments.

The strip lighting device(s) 102 in the illumination system 100 may have particular dimensions to enable a wide range of applications. For example, the lighting devices 102 may have a depth of no more than approximately 1 inch, a length of no more than approximately 25 inches, and a width of no more than approximately 4 inches. It should be appreciated that the strip lighting devices 102 may be constructed with other dimensions, and may be two-dimensional arrays of LED groups rather than one-dimensional strips. In various embodiments, the LEDs 104 are separated by a distance (e.g., 25 millimeters (mm) or 3 mm). In addition, each of the LEDs 104 may be configured to emit light with the same or different characteristic (e.g., wavelength, CCT value, etc.). As shown in FIG. 1C, the group of LEDs 104-1, 104-2, 104-3 may be disposed on the same column on consecutive strips 102 abutting one another. Alternatively, with reference to FIG. 1D, the two LEDs 104-2, 104-3 may be disposed next to each other on the same strip 102 while the LED 104-1 may be disposed next to one of the LEDs 104-2, 104-3 but on a different strip.

The LEDs 104 may be operated individually or in a grouped manner. For example, each LED may be independently coupled to the control circuitry 112 such that the control circuity 112 can separately control individual LEDs. Alternatively, some of the LEDs 104 may be wired together to allow the control circuitry 112 to control them as a single unit; different groups may or may not share one or more LEDs 104.

Figure 2A:
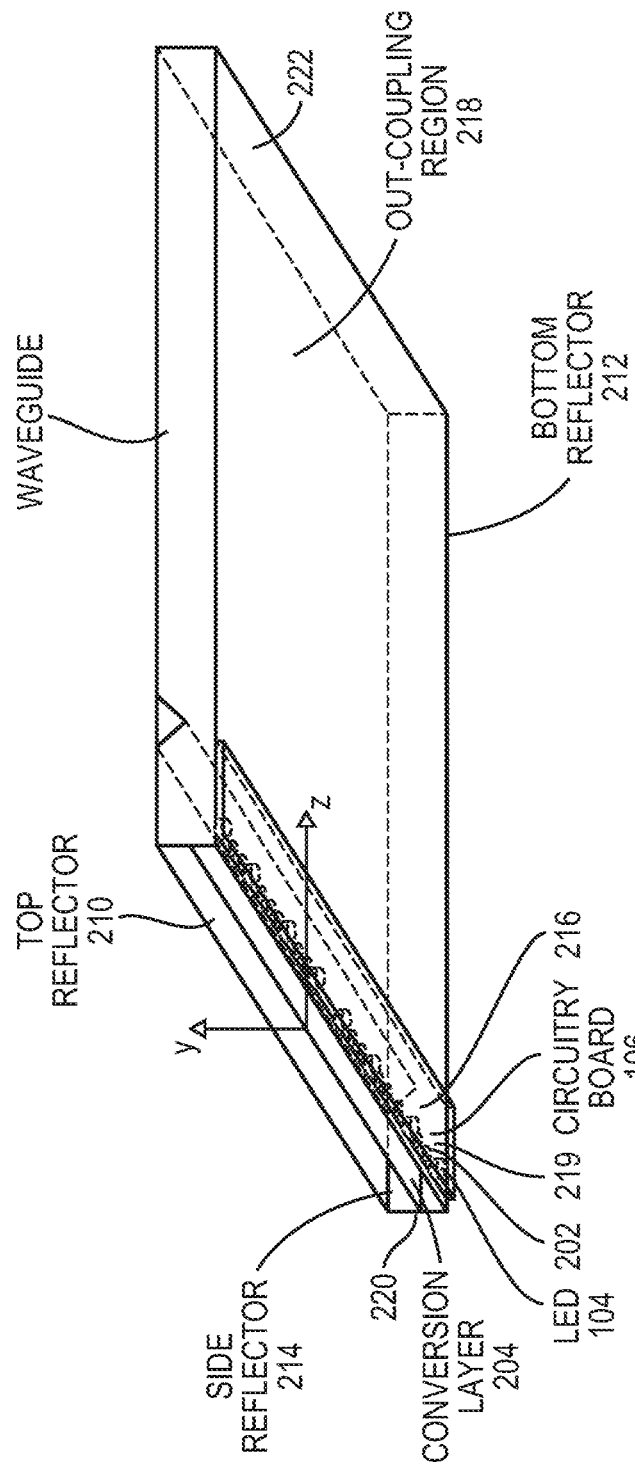
FIG. 2A schematically depicts an exemplary three-dimensional configuration of an illumination system in accordance with various embodiments.

With reference to FIG. 2A, in some embodiments, light emitted from the LEDs 104 travels through the space of a surrounding cavity 202 and is incident upon one or more conversion layers 204 that include one or more photoluminescent materials (e.g., phosphors, quantum dot materials, etc.) for converting the LED light. The conversion layer(s) 204 absorbs at least some of the light emitted from the LEDs 104 and re-emits at least some of the absorbed light in a spectrum containing one or more wavelengths that are different from the absorbed light. In various embodiments, the photoluminescent material(s) contained in the conversion layer(s) 204 is chosen based at least in part on the waveguide material. In one embodiment, the conversion layer(s) 204 is constructed from a foil that includes a composition of photoluminescent materials. For example, the foil may be premade using a conventional substrate material (e.g., one or more layers of polymer such as PET) and a binder material (such as silicone); the composition of photoluminescent materials is then disposed on the substrate surface.

Figure 2B:
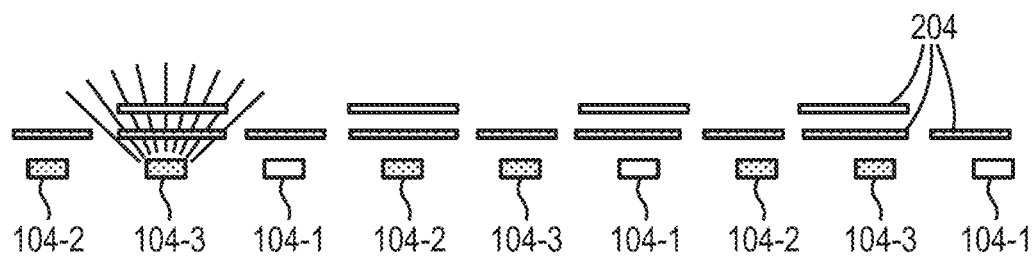
FIG. 2B depicts a spatial arrangement of LEDs and associated conversion layers for converting the wavelength of at least a portion of the LED light in accordance with various embodiments.

As shown in FIG. 2B, when multiple conversion layers 204 are used, the foils including different compositions of photoluminescent materials may be placed on top of each other with or without a gap therebetween. In one embodiment, one or more layers made of polymer can be implemented to separate the conversion layers. In addition, a second layer made of the substrate material may be applied to the conversion layer(s) 204 so as to cover the photoluminescent materials thereon. In some embodiments, the foil in the conversion layer(s) 204 includes one or more quantum dot materials. In addition, the foil may include a quantum dot enhancement film (QDEF) made by 3M Inc. or Nanoco Technology Ltd. to provide a geometry for deploying the quantum dot materials. As described above, the conversion layer(s) 204 may absorb at least some of the light emitted from the LEDs 104 and re-emit (or converts) at least some of the absorbed light in a spectrum containing one or more wavelengths that are different from (typically longer than) the light emitted by the LEDs 104. The wavelength of the converted light may depend on the composition ratio of the photoluminescent materials, the characteristics associated with each photoluminescent material, and the wavelength of the light emitted from LEDs 104.

Figure 2C:
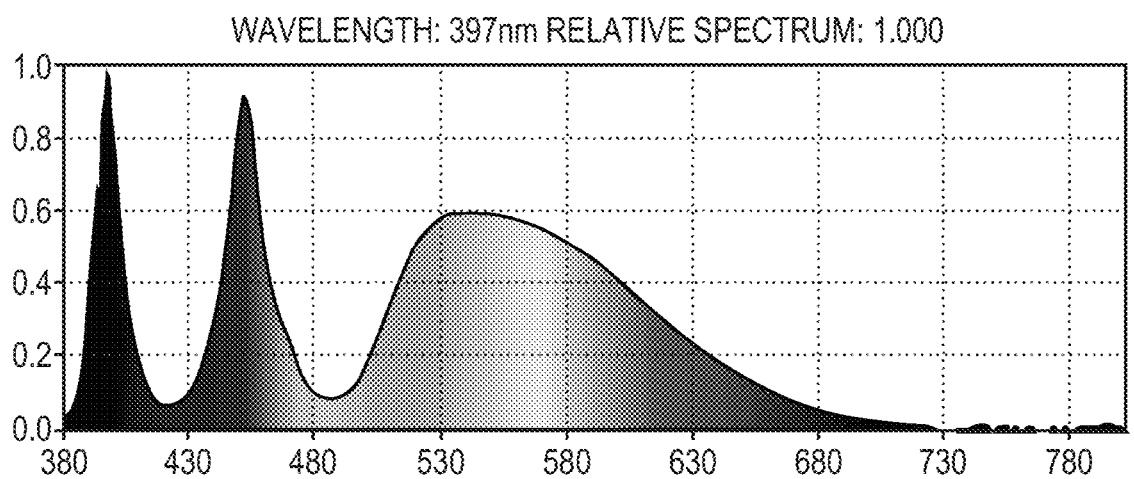
FIG. 2C shows a combined spectrum of white light and UV-A light.

The planar remote phosphor architecture illustrated in FIG. 2A, wherein light emitted from the LEDs 104 travels through the surrounding cavity 202 before interacting with the conversion layer(s) 204, facilitates selective mixing so that, for example, the output of blue-emitting LEDs interacts with the conversion layer(s) 204 and provides white light via mixing of the yellow converted light with the unconverted blue light. As a result, the CIE 1931 color coordinates of the resulting white light are shifted to the green region. The UV-A light, with a peak wavelength in the range of 380 nm to 420 nm, influences the color coordinates to a much greater degree than shorter wavelengths. The combined spectrum of the white light combined with this UV-A light is shifted toward the blue region as shown in FIG. 2C.

Figure 2D:
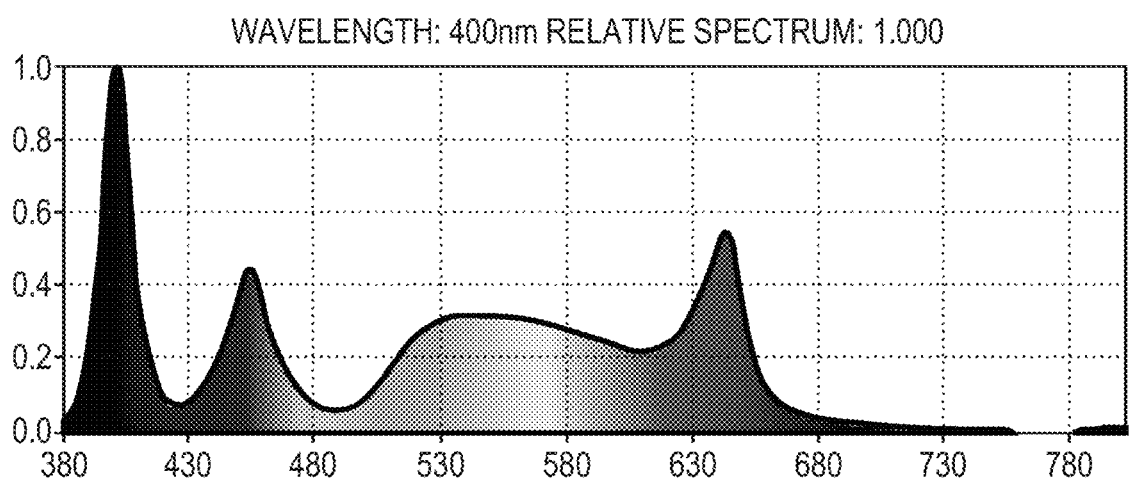
FIG. 2D shows a shift of the spectrum of FIG. 2C toward the red end to achieve a desired CCT with good color consistency.

When the planar remote phosphor architecture illustrated in FIG. 2A includes red-emitting LEDs, the white light color coordinates are shifted toward the red end of the spectrum as shown in FIG. 2D. By adjusting the amount of red light contributing to the mix and/or the photoluminescent material and its density, it is possible to obtain a desired CCT with good accuracy and color consistency (e.g., below 3 standard deviation color matching (SCDM) units). This arrangement also results in a high color rendering index (CRI) of, e.g., 85 or greater because the UV-A light does not contribute much to color perception of the light. As is well known, CRI values (which are independent of color temperature) range from 0 to 100 and light sources with CRI values of 80 or above are considered to have good color-rendering capacity. While the CRI of the spectrum shown in FIG. 2C is 66.5, the CRI of the spectrum shown in FIG. 2D, which includes red LED light, is 86.2. The red light, in other words, improves color perception.

Figure 3A:
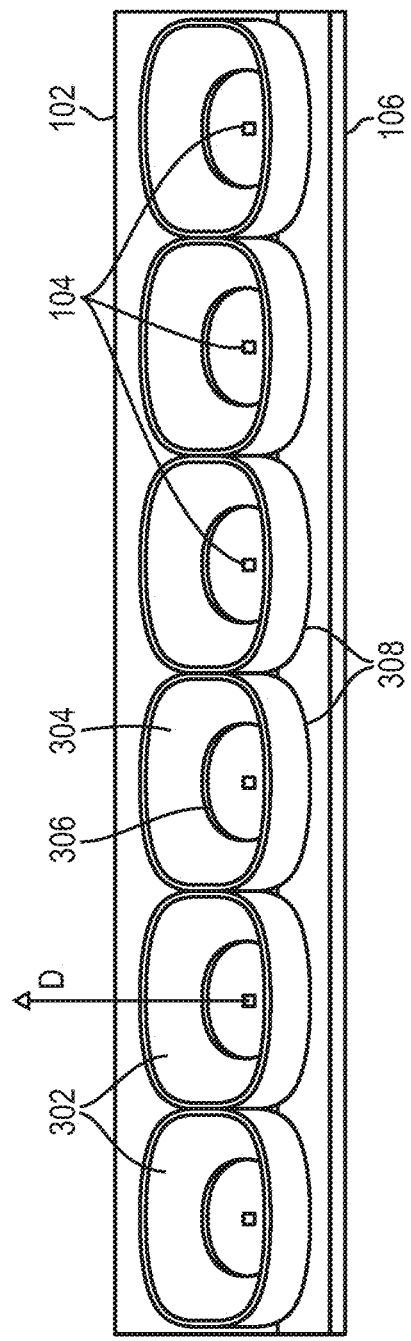
FIGS. 3A and 3B depict an implementation of reflectors surrounding the LEDs in an illumination system in accordance with various embodiments.

The light emitted from an LED 104 may interact with the photoluminescent material(s) disposed above a neighboring LED, cause a "crosstalk" interaction, and thereby result in additional colors. To reduce the crosstalk interaction, with reference to FIG. 3A, each LED 104 in the strip lighting device 102 may be surrounded by a cup-shaped reflector 302. As shown, each cup-shaped reflector 302 typically has a top aperture 304 and a bottom aperture 306; the LED 104 is disposed inside of the bottom aperture 306. The shapes of the apertures 304, 306 may be, for example, circular, elliptical, rectangular, square, etc., and may be the same or different from each other. In one embodiment, the reflectors 302 abut each other such that the bottom portions 308 thereof form a continuous surface. The reflectors 302 may be made of a high reflectivity material, such as MS-2002 silicone from DOWSIL.

In some embodiments, the geometry of the cup-shaped reflectors 302 is configured to provide a uniform distribution of the light intensity at a specific distance, D, above the LED 104 where the conversion layer(s) 204 is typically disposed. In one embodiment, the reflector 302 is a parabolic reflector (i.e., a reflecting optic whose reflective surface forms a truncated paraboloid), and the LED 104 is placed at or near the focus of the paraboloid. Thus, a light beam emitted from the LED 104 onto the reflector 302 may be redirected upward for at least partial collimation of the beam.

Figure 3B:
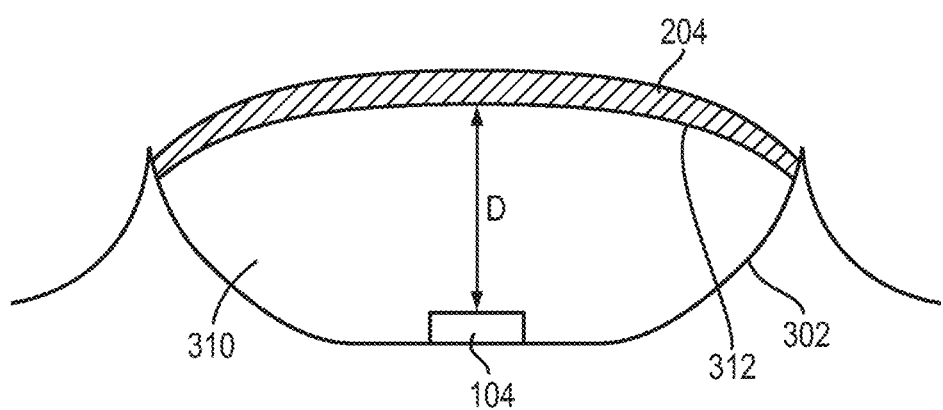

Referring to FIG. 3B, in various embodiments, an encapsulant material is potted over the LED 104 within a cavity space 310 created by the reflector 302 to at least partially encapsulate the LED 104. In one embodiment, the height of the encapsulant material above the LED 104 approximately corresponds to the specific distance D described above, thus the light intensity on the top surface 312 of the cavity space 310 may be uniformly distributed without having any visible high intensity spots thereon. The encapsulant material may include, consist of, or consist essentially of a clear material such as silicon. Alternatively, the encapsulant material may form a cover having a convex or domed shape on top of the reflector aperture 304; the cavity space 310 can be filled with air, gas such nitrogen, or instead can be under vacuum. In addition, one or more conversion layers 204 including one or more types of photoluminescent materials (e.g., phosphors, quantum dot materials, etc.) may be coated inside and/or outside the top surface 312 of the encapsulant material to convert the light emitted from the LEDs 104 as described above. In some embodiments, the cavity space 310 is at least partly filled by the encapsulant material that includes a composition of the photoluminescent material(s) and waveguide material so as to allow the photoluminescent material(s) to be embedded in the waveguide material.

With renewed reference to FIG. 2A, in one embodiment, the cavity 202 formed between the circuit board 106 and the conversion layer(s) 204 is filled with a waveguide material (e.g., silicone) such that the waveguide material is in direct contact with the top surface of the circuit board 106 and the conversion layer(s) 204. In addition, one or more reflectors 210-214 may be disposed on the top, bottom and/or side surfaces of the waveguide, respectively, such that the light emitted from the LEDs 104, including both unconverted and converted light by the conversion layer(s) 204, can be mixed inside a mixing region 216 of the waveguide; the mixed light then propagates to an output region 218 of the waveguide for outputting the light. In addition, a reflector 219 may be disposed on the top surface of the circuit board 106. In one embodiment, at least one of the reflectors 210-214, 219 is made of a high-reflectivity silicone (e.g., CI2001 from DOWSIL). Alternatively, a high-reflectivity foil may be used as one or more of the reflectors 210-214, 219. It should be noted that although FIG. 2A depicts the LEDs 104 and conversion layer(s) 206 disposed on one side 220 of the waveguide only, they may be disposed on another side 222 with the similar spatial arrangement. In addition, the location of the output region 218 may be anywhere on the other LEDs 104-1, 104-2, 104-3. These groups repeat in a linear sequence along a PCB $410_1$. In one embodiment, the LEDs 104-1 are red and the LEDs 104-2 and 104-3 are both blue (although they may be different LED types). In the configuration presented in FIG. 5C, two types of LED emitting UV-A light (e.g., at different wavelengths), 104-U1 and 104-U2, are connected in series together with LEDs 104-1—in the top row, LEDs 104-U1 are used and in the third row, LEDs 104-U2 are used. The alternate (second and fourth) rows consist entirely of a single UV or non-UV LED type. This configuration allows each row to be driven by a single channel and collectively produces white light through the phosphor while also providing UV-A light.

Figure 1D:
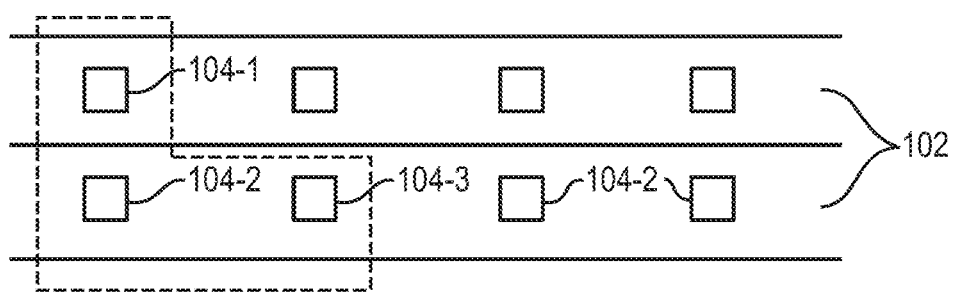

The illustrated linear sequence is only one example of groupings, however; in other implementations, the groupings are spread across linear LED sequences as shown in FIGS. 1C and 1D.

Suitable LEDs are as follows:

|  | 104-U1 | 104-U2 | 104-3 | 104-2 | 104-1 |
|---|---|---|---|---|---|
| LED | LxF3-U390100007001 | LHUV-0405-A070 | SB1515NS | SB1515NS | LXZ1-PD02 |
| Peak Wavelength [nm] | 395 | 405 | 450 | 450 | 630 |
| Radiant Power [mW] | 750 | 750 | 900 | 900 | 350 |
| Current [mA] | 500 | 500 | 500 | 500 | 500 |
| Forward Voltage [V] | 3.1 | 3.1 | 3 | 3 | 2.2 |
| Number of LEDs | 8 | 4 | 4 | 8 | 6 | waveguide and is not limited to the top surface of the waveguide as depicted in FIG. 2A.

In one implementation, the entire circuit board 106 is encapsulated inside the waveguide; the illumination system 100 may include a heat-conducting path connecting the bottom surface of the circuit board 106 to an outer surface of the waveguide for dissipating heat generating by the LEDs 104. In one embodiment, the heat-conducting path is formed by using a heat conductive material as a part of the waveguide material and disposing the circuit board 106 to be in directly contact with the waveguide.

As discussed above, the LEDs 104 mounted on the circuit board 106 may be controlled individually or in a group manner to generate light having a tunable CCT value within a range. In some embodiments, the control circuitry 112 adjusts the intensity of the light emitted from one or more of the LEDs 104-1, 104-2, 104-3 by varying the amplitude and/or duty cycle of the current and/or voltage associated therewith. In addition, the control circuitry 112 may include a look-up table that maps particular target CCT values to a set of intensity ratios for the LEDs within the LED array. Thus, when the control circuitry 112 receives information indicative of a desired CCT value, it may access the look-up table to retrieve the corresponding intensity ratios, and, based thereon, adjust the intensities of the LEDs.

Figure 4A:
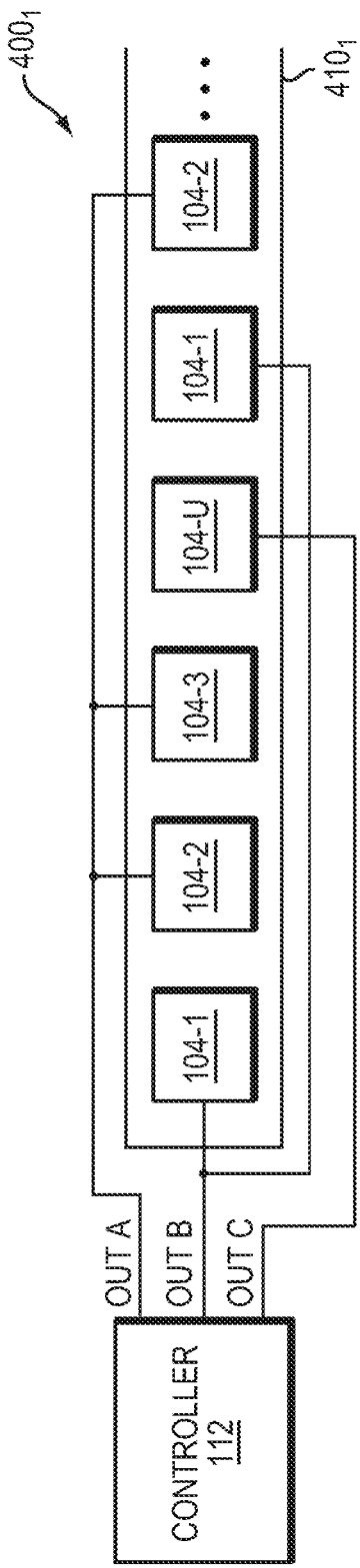
FIG. 4A depicts an exemplary LED configuration including groups of red, blue, and UV-A LEDs combined in series.
Figure 4B:
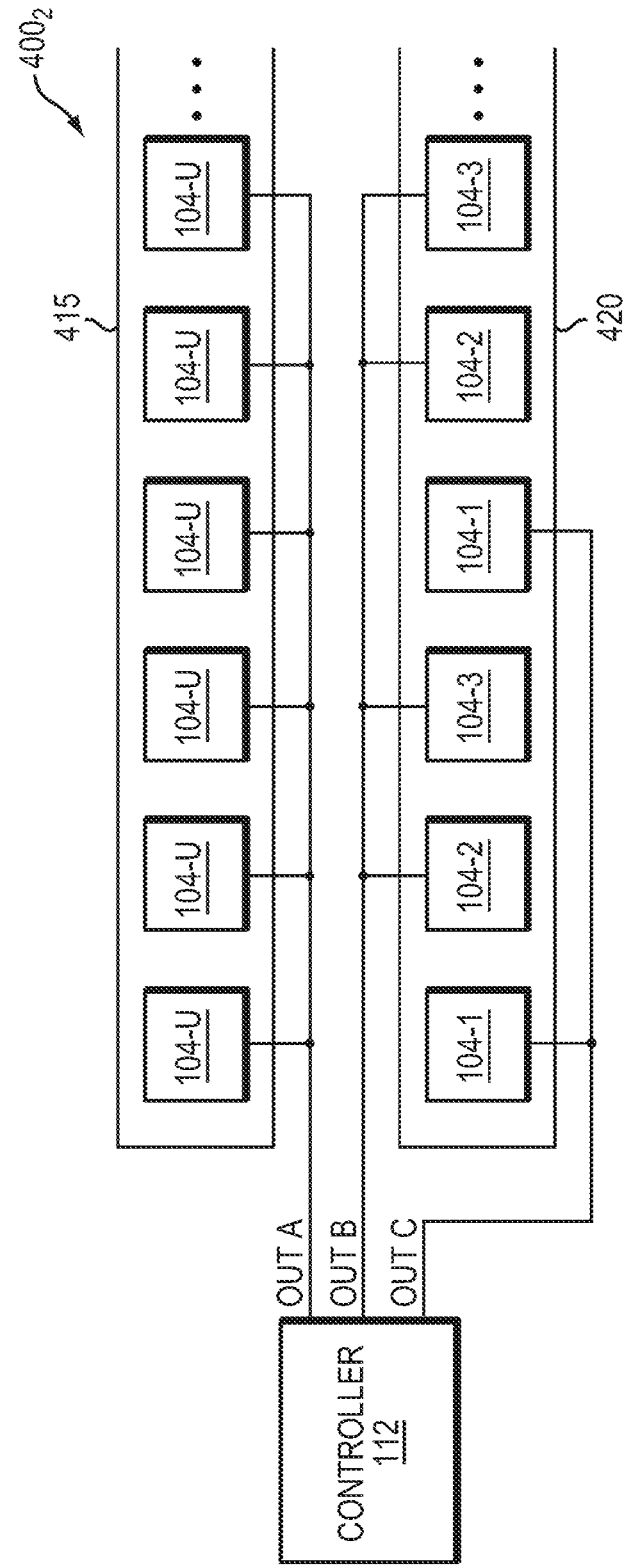
FIG. 4B depicts an exemplary LED configuration including groups of red and blue LEDs in one series and an adjacent series of UV-A LEDs.
Figure 4C:
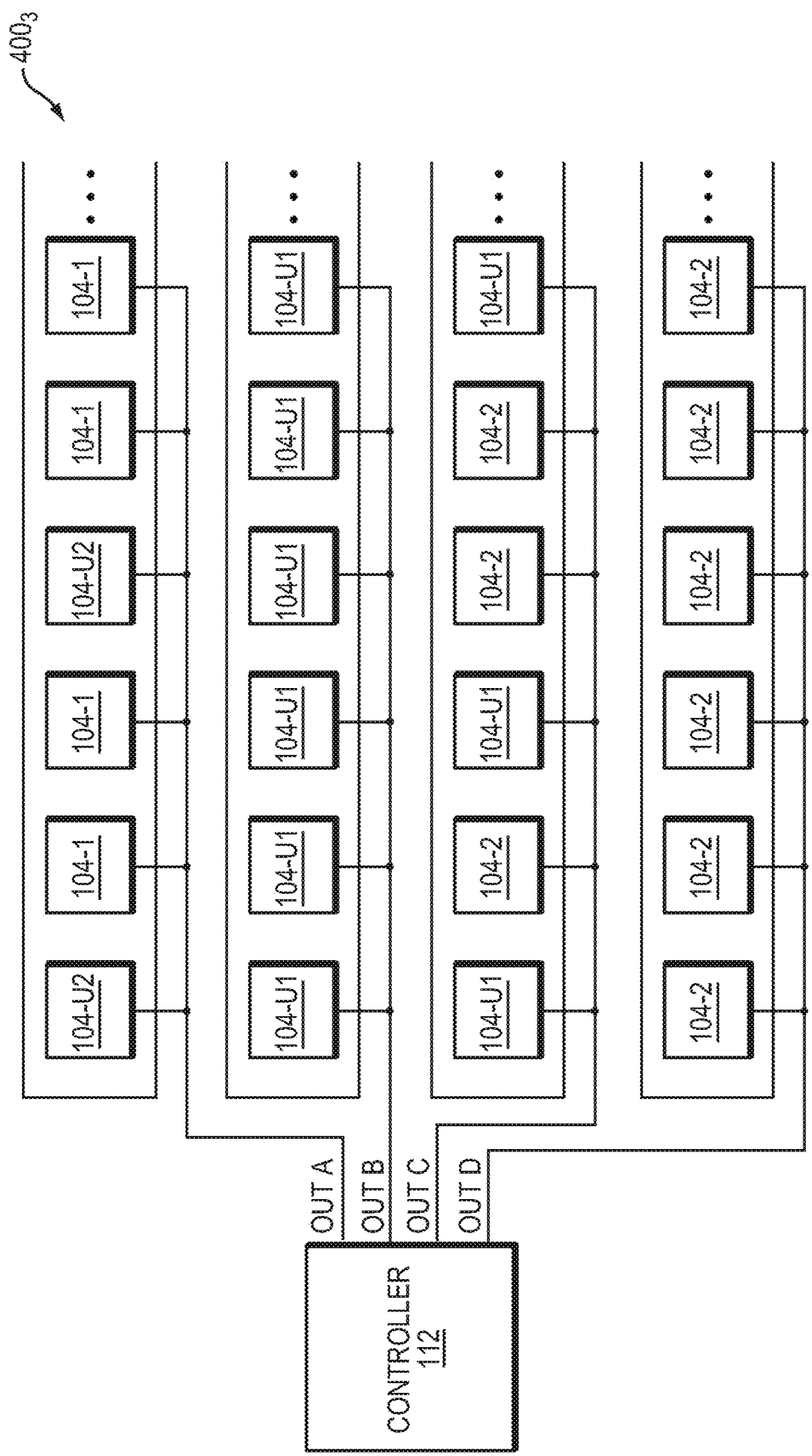
FIG. 4C depicts an exemplary LED configuration including red and blue LEDs and two types of UV-A LEDs.

Refer now to FIGS. 4A-4C, which illustrate representative configurations $400_1$, $400_2$ for combining germicidal UV-A light with light in the visible range to create white light with a desired CCT value. Although the term UV-A commonly refers to the wavelength region 315-400 nm, for purposes of this specification UV-A refers to the broader wavelength region 315-420 nm. In the configuration $400_1$, LEDs 104-U emitting UV-A light are grouped with three In some embodiments, the controller 112 has three output channels A, B, C. Channel A controls the blue LEDs, channel B controls the red LEDs, and channel C controls the UV-A LEDs. Once again, the control circuitry 112 adjusts the intensity of the light emitted from one or more of the LEDs 104-1, 104-2, 104-3, 104-U by varying the amplitude and/or duty cycle of the current and/or voltage associated therewith. In some embodiments, only the amplitude and/or duty cycle of the visible-light LEDs 104-1, 104-2, 104-3 is controlled; in other embodiments, the amplitude and/or duty cycle of all LEDs is controlled.

In the configuration $400_2$ shown in FIG. 4B, the UV-A LEDs are deployed on a single printed circuit board (PCB) 415, and the LEDs 104-1, 104-2, 104-3 are deployed on an adjacent PCB 420, both of which are controlled by the controller 112. The lighting system may include a sequence of PCBs 415, 412, e.g., alternating or present in different quantities (e.g., two or three PCBs 420 for every PCB 415).

The conversion layers with photoluminescent materials may be disposed above some or all of the LEDs, and following conversion, light from all LEDs is mixed in the waveguide as described above. For example, blue light or UV-A light may interact with phosphor material, and some of it is converted to a different color. The converted light and the remaining blue light are mixed with the red and UV-A light and extracted out from the waveguide plate to form white light illumination. The red light is used to tune the white light color coordinates to fit the required CCT and to improve CRI values, so it may be necessary to control the amplitude and/or duty cycle only of the red LEDs 104-1. Additional white LED at a specific CCT, may be assembled on the PCB to enable True Tunable White (TTW) functionality—i.e., the ability to tune the CCT along the black-body curve of white light from deep warm (e.g., 1800 K) to far cool (e.g., 6500 K) with small deviation, i.e., below 1 Macadams ellipse).

Figure 5:
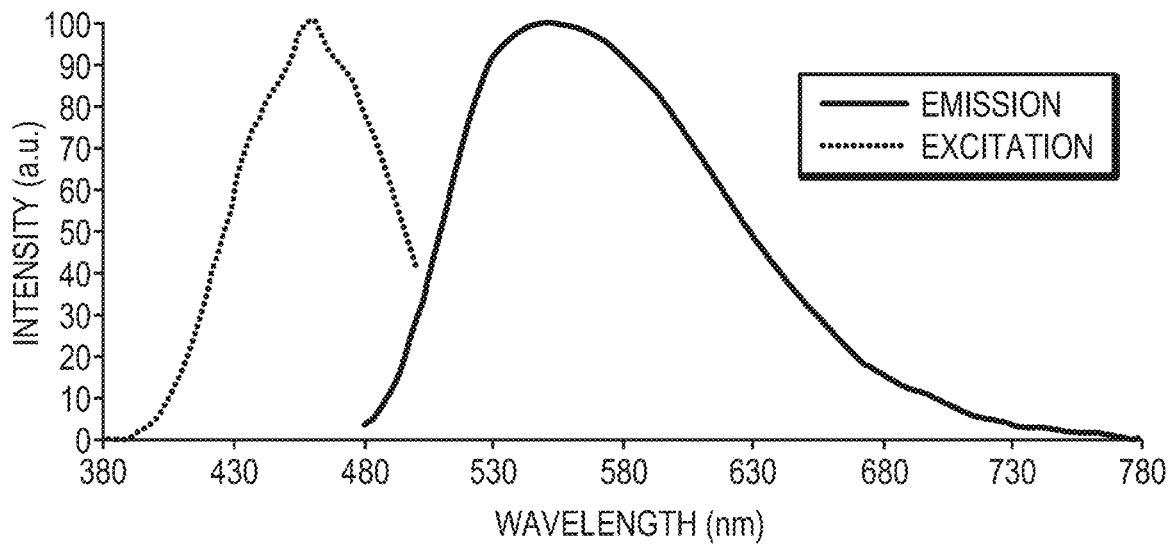
FIGS. 5 and 6 graphically depict excitation and emission spectra for photoluminescent materials useful in connection with embodiments of the invention.
Figure 6:
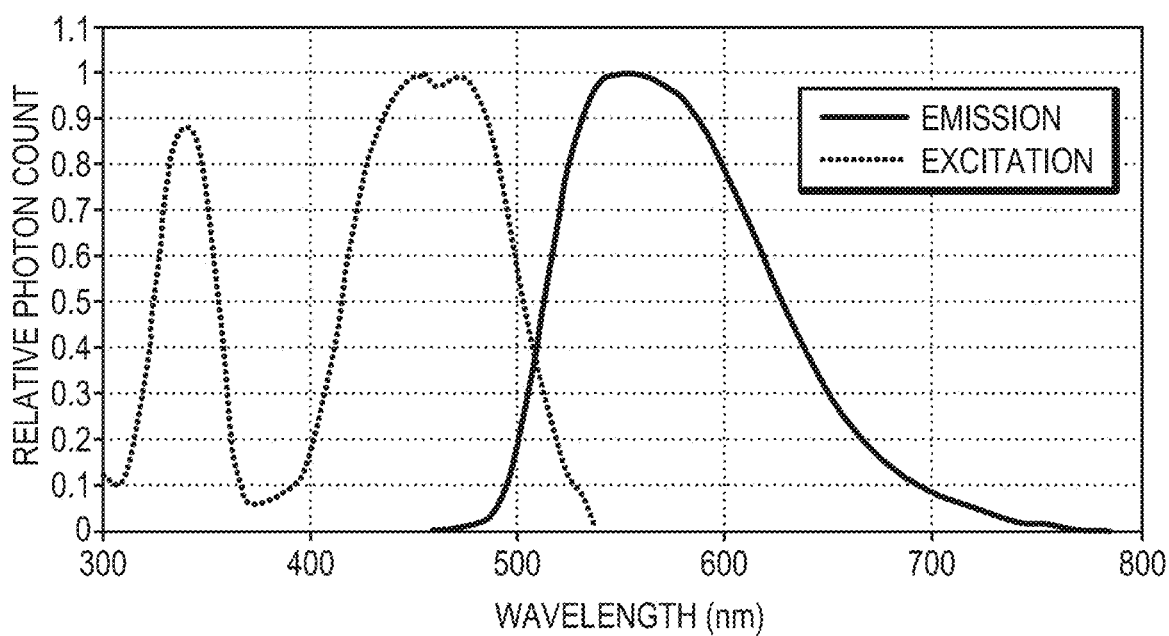
Figure 7:
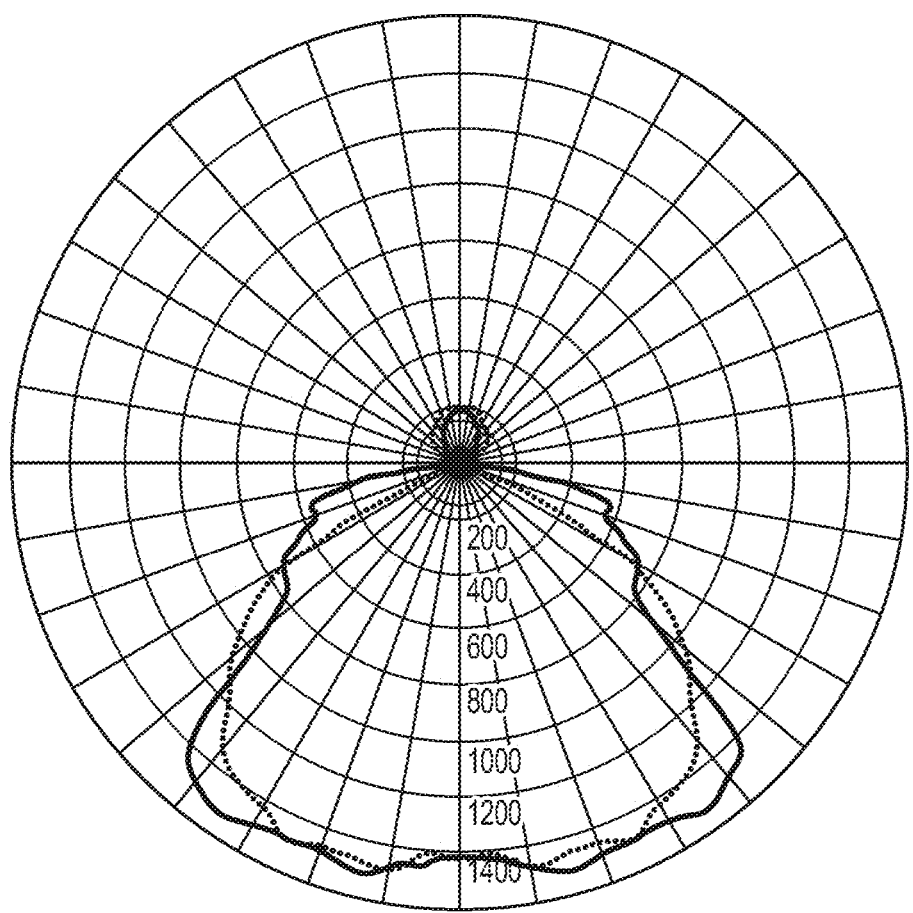
FIG. 7 depicts a representative angular UV-A light distribution from a luminaire based on an embodiment of the present invention.

The UV-A light may interact with the photoluminescent material and increase the amount of converted light. This will change the CCT of the light. In this case the intensity of the red light may be increased to shift the color coordinates to fit the required CCT. One option is to use a photoluminescent material having a very low excitation level at the UV-A wavelength (e.g., Yttrium Aluminum Oxide:Cerium $Y_3Al_5O_{12}$:Ce), as shown in FIG. 5. In this case, the photoluminescent material will convert less UV-A light to a different color. A second option is to have the phosphor excitation wavelength include the UV-A wavelength as shown in FIG. 6 (e.g., Yttrium Aluminum Garnet "537 nm"). In this case, the photoluminescent material will convert more UV-A light to a different color. In implementations where the UV-A LEDs are connected and driven together with the blue or the red LEDs when the system is operated to provide white light, some of the UV-A light will be converted and will change in CCT. In order to maintain the target CCT, the ratio of the red and blue light may be changed. In order to retain an intense UV-A emission, it is desirable to choose a wavelength that does not interact much with the phosphor material. However, placing the UV-A LEDs in the blue channel will reduces the blue light intensity and therefore the converted light. In that case it is preferable to use UV-A LEDs that exhibit greater interaction with the phosphor material in the red channel together with the red LEDs so their light will collectively increase the amount of converted light while increasing the red:blue ratio for maintaining the target CCT.

Figure 8:
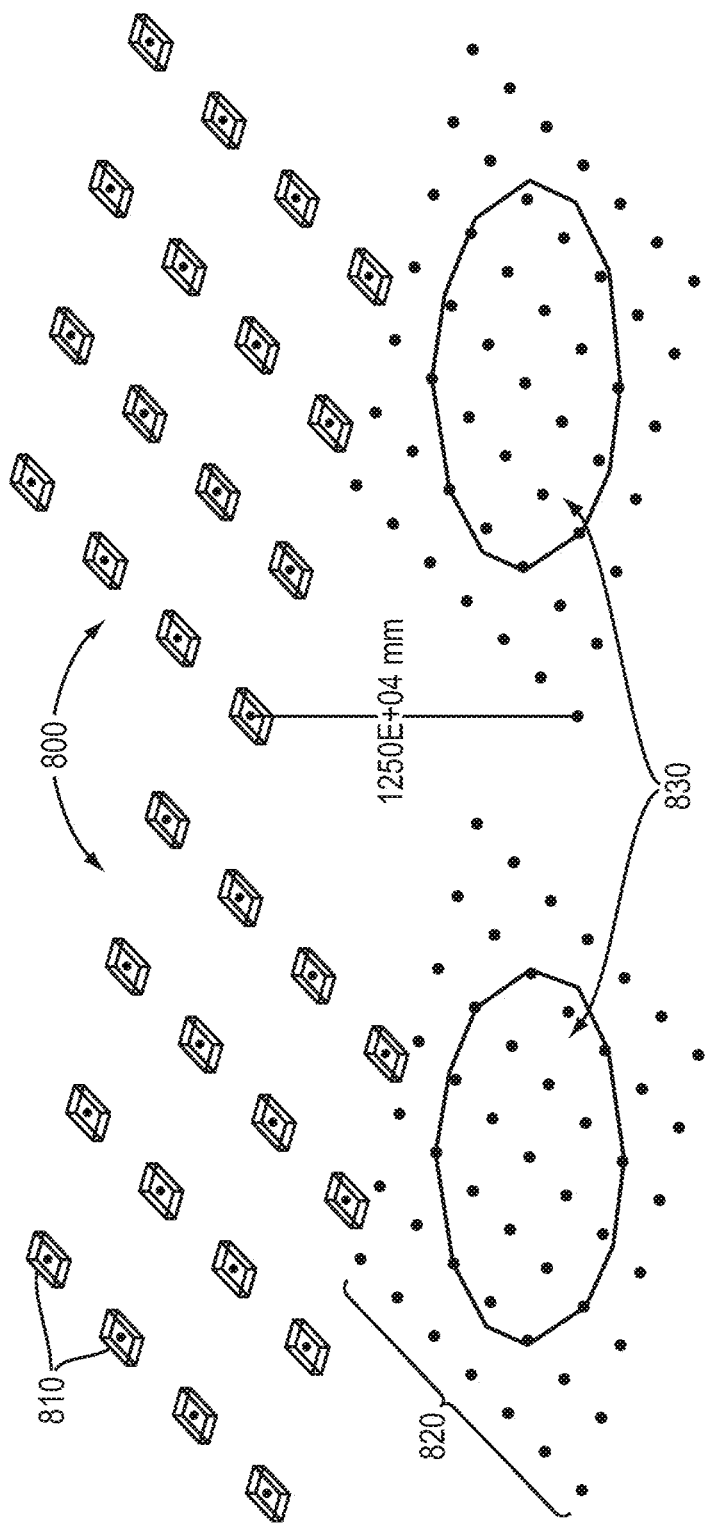
FIG. 8 illustrates the UV-A distribution over a room-size space of an array of luminaires.

The LED configurations 400 can be organized into a lighting fixture or "luminaire." In a "normal" mode of operation, the luminaire can provide conventional white light and germicidal UV-A light. For example, the UV-A emission may be ~7 W together with the required intensity of white light. As shown in FIG. 8, each luminaire may, in some embodiments, provide white light over a wide coverage area but UV-A light over a restricted angular range. FIG. 8 illustrates how this permits a ceiling arrangement 800 of luminaires 810 to illuminate a room-size area 820 with white light but focus UV-A energy on a smaller target area 830. In particular, the luminaires may operate in a "boost" mode in which the red and UV-A LEDs are active and at least the latter operated at maximum power, and the blue LEDs are not active; for example, with reference to FIG. 4A, only output channels B and C are active. As a result, the UV-A intensity (or irradiance in $W/m^2$) in boost mode may be three times that in normal mode, and may exceed the maximum safe intensity (or irradiance) for human exposure. The red light provides a visual indication of danger.

Operating illumination that includes UV light should comply with safety regulations such as the IEC 62471 standard, which covers photobiological safety of lamps and lamp systems. According to this standard, near-UV emission with irradiance values below 10 $W/m^2$ is exempt from any exposure time limitation. Illumination devices in accordance with embodiments hereof use a planar structure that emits the light uniformly from the planar out-coupling area. In this case, the total radiant flux from the illumination device divided by the area of the planar out-coupling area should provide an irradiance value below the regulatory maximum. For example, if the planar out-coupling area is 0.6 m×0.6 m=0.36 $m^2$, then the total maximum radiant flux is 3.6 W, which results in a maximum irradiance of 10 $W/m^2$.

Figure 9A:
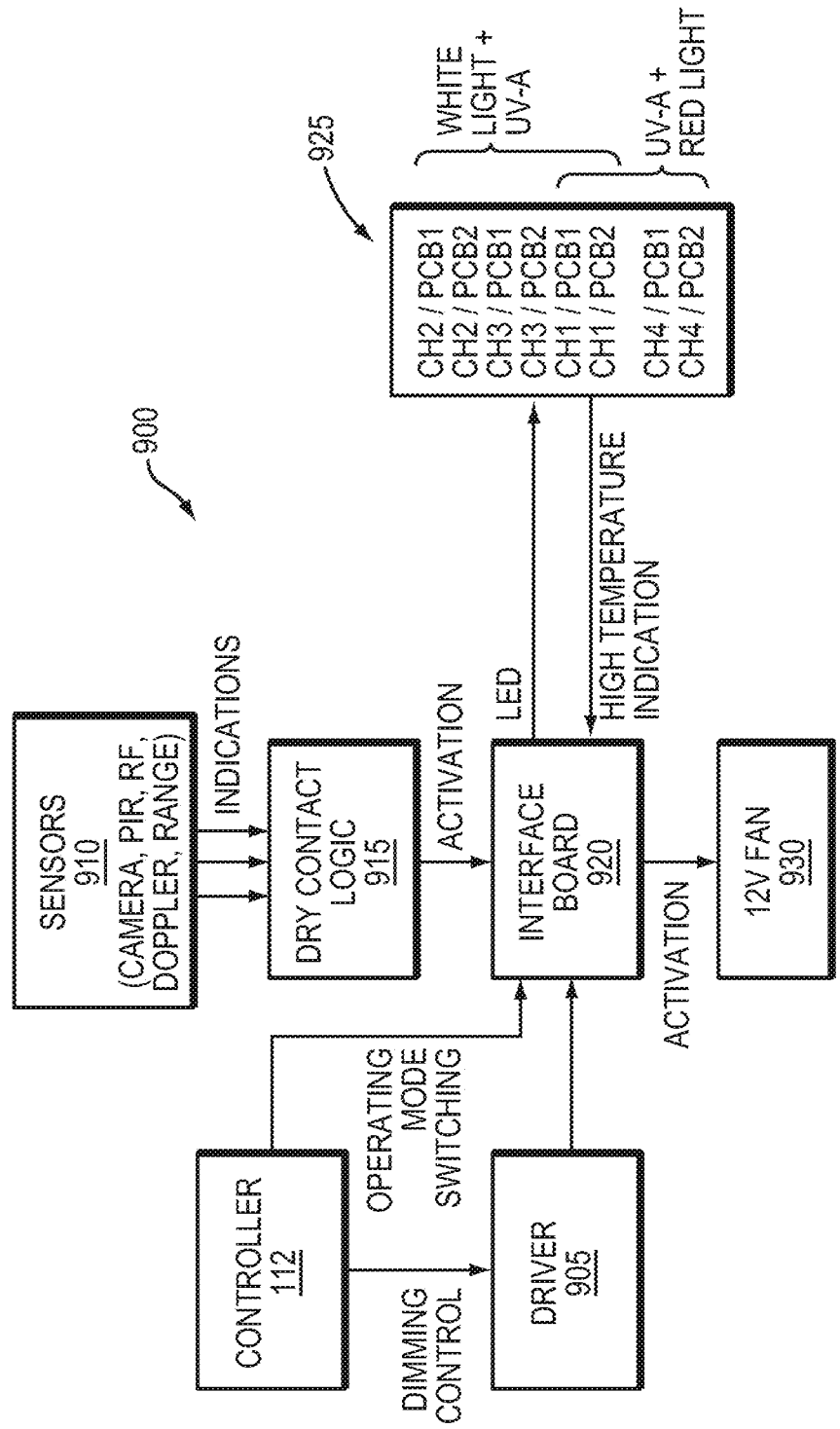
FIGS. 9A and 9B schematically illustrate, respectively, a representative control circuit for driving one or more luminaires in normal and "boost" modes and a switch matrix for toggling between the two states.

Representative circuitry 900 for controlling an illumination system with these features is shown in FIG. 9A. All or various components of the circuitry 900 may be combined into a single module 112 or, as illustrated, the controller 112 may be one component of the circuitry 900. In the illustrated embodiment, the controller 112 performs the functions described above as well as selecting the operating mode (e.g., normal or boost), dimming the white output light in accordance with a stored program or user commands (e.g., by controlling the voltage and/or current output of the LED driver circuit 905), and/or tuning the color temperature of the output light. One or more sensors 910 receive environmental information relevant to the operation of the lighting system. For example, the sensors 910 may be or include occupancy sensors (such as passive infrared (PIR) sensors, ultrasonic sensors, cameras, RF sensors, Doppler sensors, etc.) or other sensors associated with a relevant environmental condition. The outputs of these sensors are received by logic 915 that determines an action to be taken, e.g., to switch the operating mode of the lighting system. For example, boost-mode operation, or any operational mode involving UV-C, may be permitted only when no personnel are detected in the region 830 or even in the room 820.

The action selected by logic 915 may be to change the current activation pattern of LEDs. This is effected by an interface board 920, which contains a switch matrix for controlling the LEDs 925 associated with a single room or with multiple rooms of a facility. The interface board 920 may also receive commands from the controller 112 to change the current activation pattern. Finally, the interface board 920 may receive feedback from the LEDs 925, e.g., their operating temperature (which may be communicated by temperature sensors on the LED boards), and may take an action, such as activating or deactivating a cooling fan 930 for the LEDs. Logic 915 may be configured to, for example, change the operating mode in response to signals from, e.g., two independent sensors 910 indicating the absence of personnel in the room 820. Requiring mutual corroboration between two independent sensors before the lighting state is changed avoids actions based on spurious or transient sensor readings. Particularly if the boost state is accompanied by the red warning light, the chance of harm to humans is small.

Figure 9B:
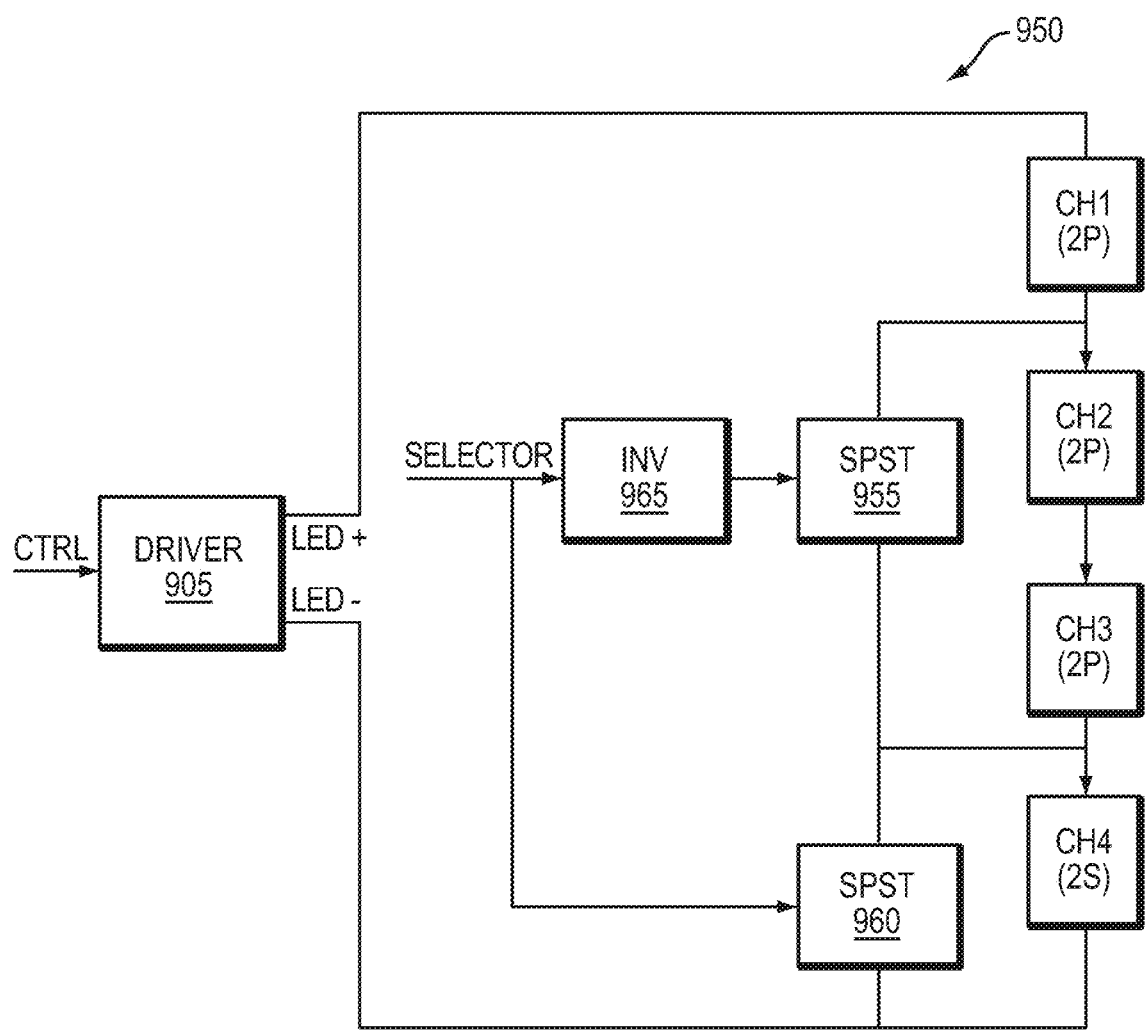

An illustrative configuration 950 of the interface board 920 is shown in FIG. 9B. A pair of "dry" SPST switches (e.g., relays) 955, 960 control the LED sets or channels CH1, CH2, CH3, and CH4. The dry switches 955, 960, in turn, are controlled by a selector signal that passes through an inverter 965 to the switch 955 but passes unchanged to the switch 960. Each LED channel may control one or more boards with identical LED populations. In one embodiment, channel CH1 includes red LEDs with a small number of UV-A LEDs; channel CH2 and CH3 contain LEDs that create white light, e.g., which individually emit blue or white light; and channel CH4 contains only UV-A LEDs. As a result, as shown in FIG. 9A, operating CH1, CH2, and CH3 produces white light with some UV-A radiation and some red light to achieve a desired color temperature. This is normal mode. In boost mode, all UV-A LEDs and all red LEDs are operated.

Thus, a positive selector signal from logic 915 or the controller 112 closes the switch 960, but the inverted signal leaves the switch 955 open so that normal mode is achieved: the drive current is shorted to ground above CH4, so that only CH1, CH2, and CH3 receive power. A negative selector signal, corresponding to boost mode, provides a low-resistance path around CH2 and CH3 so that only CH1 and CH4 are operated. In order to use the same LED driver 905 in this configuration, the voltage drop for CH2 and CH3 should be close to the voltage drop for CH4.

The control circuitry 112 may include or be connected to one or more modules implemented in hardware, software, or a combination of both. For embodiments in which the functions are provided as one or more software programs, the programs may be written in any of a number of high level languages such as PYTHON, FORTRAN, PASCAL, JAVA, C, C++, C#, BASIC, various scripting languages, and/or HTML. Additionally, the software can be implemented in an assembly language directed to the microprocessor resident on a target computer; for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

Figure 10A:
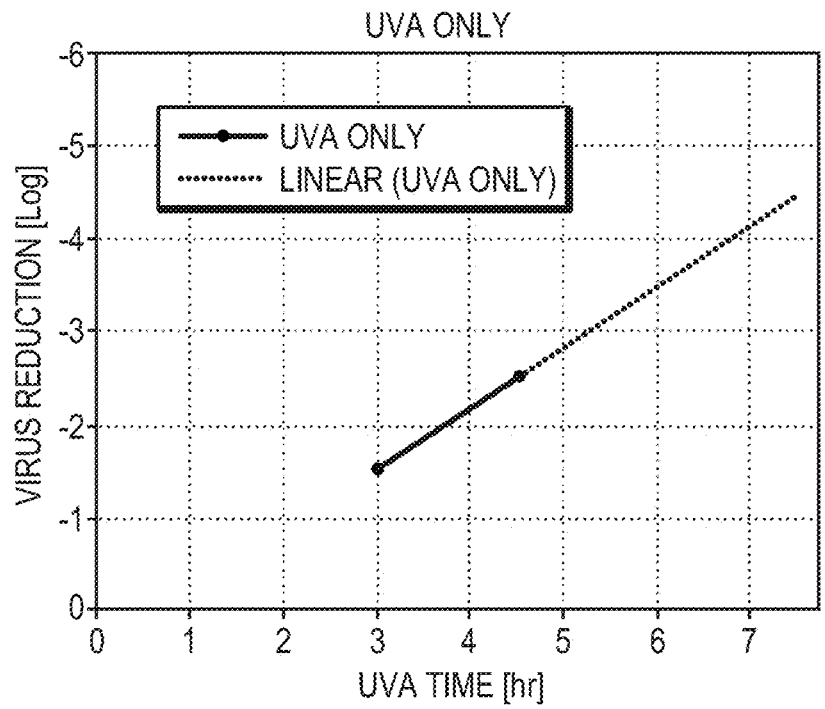
FIG. 10A plots virus reduction (as a logarithm) against the time of exposure to UV-A radiation.
Figure 10B:
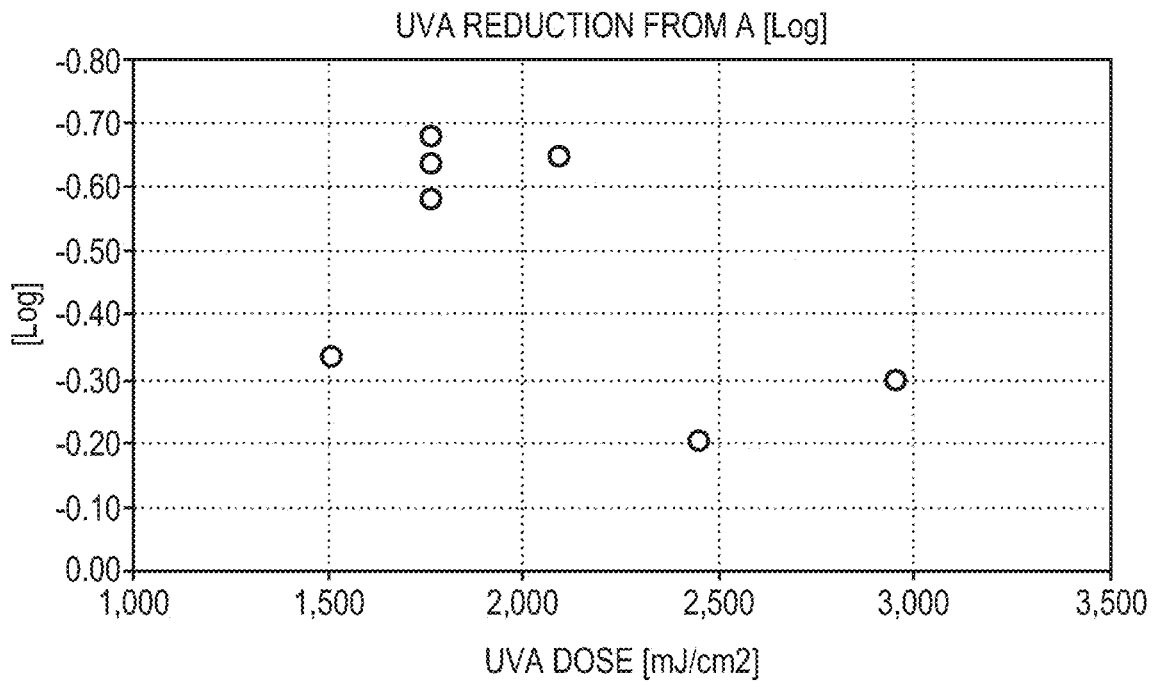
FIG. 10B depicts measurements of bacteria reduction (as a logarithm) resulting from various UV-A radiation dose levels in a hospital patient's room.
Figure 10C:
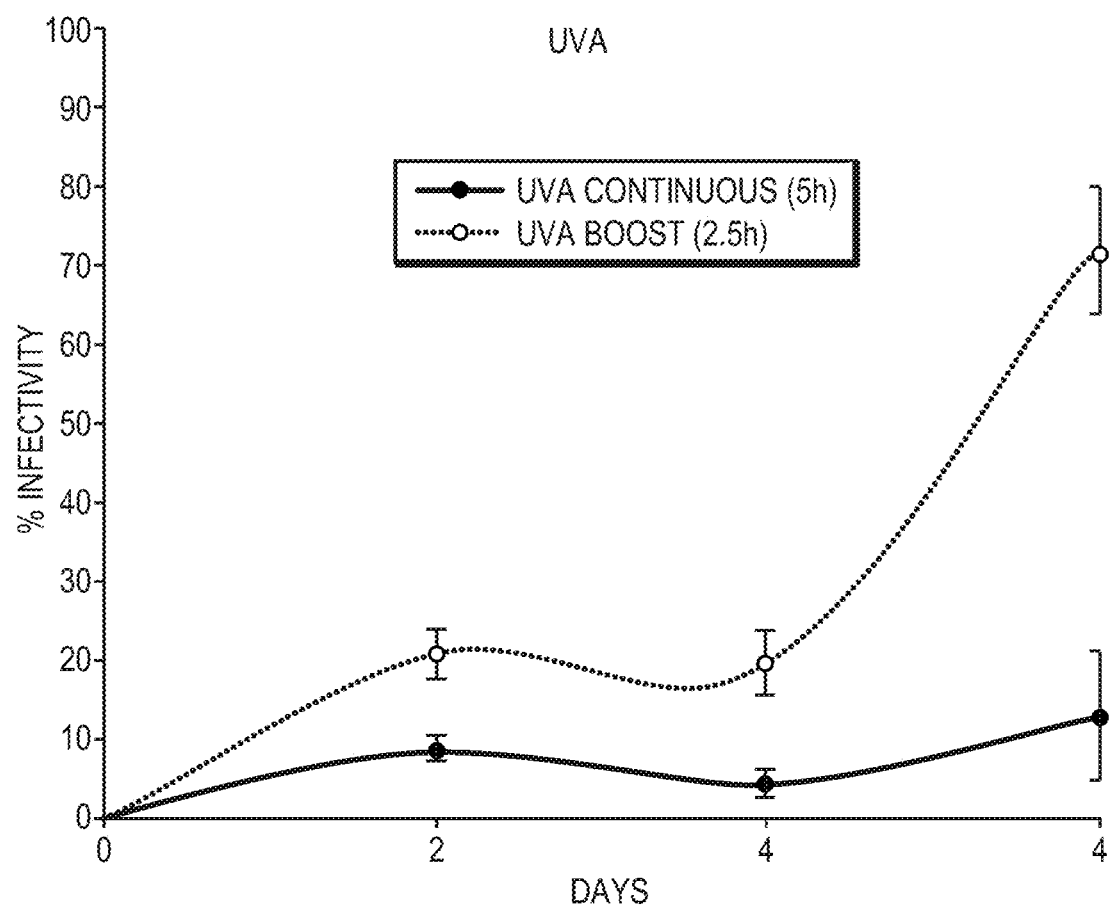
FIG. 10C plots infectivity over a period of days following exposure of viruses to UV-A radiation at a moderate power level for 5 hours and at a higher power level for 2.5 hours.

The effectiveness of embodiments of the invention in reducing pathogen levels and their infectivity is illustrated in FIGS. 10A-10C. FIG. 10A shows analyses of data obtained in a test where SARS-CoV-2 pseudoviruses was exposed to UV-A radiation at 0.6 W/m² for 5 hr and 7.5 hr. The raw results are as follows:

| Test # | Time [Hr] | Pathogen reduction [Log] |
|---|---|---|
| 1 | 5 | −1.57 |
| 2 | 7.5 | −2.55 |

FIG. 10A shows extrapolation of the exposure time necessary to achieve virus reduction above 99.9% (log=−3). This confirm the ability of UV-A light to achieve high levels of virus redaction.

FIG. 10B shows the population reduction or pathogens such as bacteria, yeasts and molds, at various sampling points in a hospital patient's room after 8 hours of exposure to UV-A radiation along with general illumination (white light); in particular, the UV-A LEDs were integrated inside general-lighting LED luminaires were installed in the room ceiling. The data in the table below shows the bacteria population (cfu) of samples that were taken from specific locations in the room before and after the lighting treatment.

| | Sampling location in the room | (cfu) Swab before treatment | (cfu) Swab after treatment | UVA Dose [mJ/cm²] | Results (cfu) swab [Log] |
|---|---|---|---|---|---|
| 1 | Light switch | 85 | 19 | 2,088 | −0.65 |
| 2 | Panel control unit | 65 | 15 | 1,764 | −0.64 |
| 3 | Power outlet | 39 | 18 | 1,512 | −0.34 |
| 4 | Bed Fence | 106 | 53 | 2,952 | −0.30 |
| 5 | Bede Control panel | 130 | 81 | 2,448 | −0.21 |
| 6 | Cupboard handle | 19 | 4 | 1,764 | −0.68 |
| 7 | Faucet | 46 | 12 | 1,764 | −0.58 |

FIG. 10B shows the log of the reduction in bacteria population as function of the UV-A dose, which is based on irradiance measurements of the UV-A light at each of the sampling points multiplied by the 8 hr operating time. The pathogen population (cfu) was measured by analyzing the microbiology samples taken with swabs from each of the noted locations. These results confirm that UV-A light combined with white light can achieve significant pathogen reductions in hospital rooms.

FIG. 10C illustrates the effect of UV-A radiation on viral infection using two mode of irradiation: continuous mode and boost mode. The irradiation parameters are summarized in Table 1 below.

| Operating mode | Irradiance [mW/cm²] | Time [min] | Dose [mJ/cm²] |
|---|---|---|---|
| UV-A continuous | 1.200 | 300 | 21,600 |
| UV-A boost | 3.500 | 150 | 31,500 |

The viral pathogen tested was hepatitis C virus ("HCV"). In a representative experiment, HCV virus is generated in vitro, in human liver cells. RNA is produced from plasmid DNA and electroporated the RNA into human liver cells. At day 10 post-electroporation, the viruses are secreted into a growth medium, concentrated and stored as virus stocks. To test infection, a virus stock is used to infect human liver cells in culture. Infected cells are identified by immunostaining with human serum derived from infected hepatitis C patients, followed by exposure to a secondary anti-human antibody with fluorescence signal. The infected cells are visualized under a fluorescence microscope. To titer the number of infectious viruses, a Focus Forming Unite (FFU) assay is performed, where cells are infected and the number of foci (fluorescence signal of adjacent infected cells) are counted; these represent the number of infectious viruses.

In one procedure, virus stock was diluted to $10^2$-$10^3$ infectious viruses per 30 μl well in a 96-well plate. The samples were placed inside a fume hood. Radiation was applied in the different modes noted above and the medium containing irradiated viruses was transferred to human Huh7.5 liver cells that were preseeded in a 96-tissue culture plate at $5\times10^4$ cell/well. At 2, 4 and 6 days post infection, the cells were immunostained with human serum derived from infected hepatitis C patients, followed by a secondary anti-human antibody with a fluorescence signal. The infected cells were visualized and counted using INCUCYTE Live-Cell Analysis. The infection percentage was calculated as the number of positive infected cells in each treatment compared to the number of infected cells in an untreated control.

As shown in FIG. 10C, a low level of infection was observed at day 2 post-infection. For the boost mode samples, a 20% infection was observed, while for continuous mode an infection rate of 8% was observed. The infection level declined at day 4 post-infection, probably because not all viruses that infected were viable and replicated. At day 6, the viruses that were irradiated in boost mode continued to replicate and spread, reaching 72% infection. However, a low level of infection was observed at day 6 post-infection following continuous-mode exposure (12%). These results demonstrate that irradiation in continuous mode with UV-A light damages the viruses and significantly reduces viral infection and replication.

Hence, with reference to FIG. 9A, the control circuitry 112 may ordinarily operate the LEDs to produce white light including UV-A. Upon detection of an infection event, either by personnel who issue an alert to the controller 112 or by means of suitably trained or designed sensors, the control system 112 activates the red LEDs (e.g., in a pulsed or blinking mode) to signal the need for evacuation of the area surrounding the illumination system. Once the sensor(s) 910 confirm the absence of personnel from the region that will be exposed to UV-C radiation, the control system 112 activates the UV-C LEDs for time interval sufficient to ensure pathogen eradication to the desired level. if the UV-A illumination has been active for less than threshold period, the time interval during which the UV-A illumination is active is increased accordingly to achieve the target degree of eradication. For example, the time interval may range from 1 min to 60 min. The control system 112 then de-activates the UV-C LEDs and the red LED signal, indicating the personnel are free to return to the affected area.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A lighting device producing white light having a target color correlated temperature (CCT) value and UV-A radiation, the device comprising:
    a first plurality of LEDs emitting light at a first wavelength corresponding to red light, a second plurality of LEDs emitting light at a second wavelength different from the first wavelength, and a plurality of UV-A LEDs emitting UV radiation having a peak wavelength between approximately 315 nm and approximately 420 nm;
    at least one photoluminescent material for shifting a CCT value of at least the second plurality of LEDs to produce white light; and
    a waveguide material having (i) a mixing region for mixing shifted and unshifted light so as to generate white light having the target CCT value and (ii) an output region for outputting the white light,
    wherein the output white light has a color rendering index of at least 85 and a color consistency below 3 standard deviation color matching units.

2. The lighting device of claim 1, wherein the first plurality of LEDs have an emission peak at 630 nm.

3. The lighting device of claim 1, wherein the second plurality of LEDs have an emission peak at 450 nm.

4. The lighting device of claim 1, wherein the UV-A LEDs have an emission peak at 390-410 nm.

5. The lighting device of claim 1, further comprising control circuitry for adjusting a parameter associated with at least one some of the LEDs so as to change the target CCT value of the generated white light.

6. The lighting device of claim 5, wherein the parameter comprises at least one of an amplitude or a duty cycle of a current or a voltage.

7. The lighting device of claim 5, wherein the control circuitry is configured to adjust the parameter of the first and second pluralities of LEDs to maintain the target CCT value while changing the intensity of the UV-A light.

8. The lighting device of claim 1, wherein the photoluminescent material comprises at least one of a phosphor, a quantum dot material or a fluorescent dye.

9. The lighting device of claim 1, further comprising a plurality of cup-shaped reflectors for at least partial collimation of light emitted from the LEDs, wherein each reflector has a top aperture and a bottom aperture and the bottom aperture has one of the LEDs disposed therein.

10. The lighting device of claim 9, wherein at least one of the reflectors is a parabolic reflector, the respective LED disposed therein being located at or near the focus of the parabolic reflector.

11. The lighting device of claim 10, further comprising an encapsulant material filled in a cavity space above one of the plurality of LEDs and surrounded by the respective reflector.

12. The lighting device of claim 10, wherein the reflectors comprise or consist essentially of silicone.

13. The lighting device of claim 1, further comprising at least one circuit board for mounting the LEDs thereon.

14. The lighting device of claim 13, further comprising a heat-dissipation structure thermally coupled to the circuit board for dissipating heat generated by the plurality of LEDs.

15. The lighting device of claim 1, further comprising at least one reflector located in the mixing region of the waveguide for promoting mixing of light.

16. The lighting device of claim 1, wherein the waveguide material comprises or consists essentially of silicone.

17. The lighting device of claim 1, wherein the waveguide material encapsulates at least one LED.

18. The lighting device of claim 1, wherein in the normal mode, the UV-A light has an intensity that is safe for human exposure and in the boost mode the intensity exceeds the intensity that is safe for human exposure.

19. The lighting device of claim 18, wherein in the boost mode, at least some of the first plurality of LEDs are operated to indicate a risk of harmful radiation.

* * * * *